United States Patent [19]

Sisti et al.

[11] 4,272,983
[45] Jun. 16, 1981

[54] APPARATUS FOR POROSIMETRIC MEASUREMENTS

[75] Inventors: Giorgio Sisti, Melzo; Ermete Riva, Merate; Pietro Italiano, Cernusco sul Naviglio, all of Italy

[73] Assignee: Carlo Erba Strumentazione S.p.A., Italy

[21] Appl. No.: 89,994

[22] Filed: Oct. 31, 1979

[30] Foreign Application Priority Data

Dec. 13, 1978 [IT] Italy ........................ 30787 A/78

[51] Int. Cl.³ ........................................... G01N 15/08
[52] U.S. Cl. ................................................. 73/38
[58] Field of Search ............................................. 73/38

[56] References Cited

U.S. PATENT DOCUMENTS

| | | | |
|---|---|---|---|
| 3,371,519 | 3/1968 | Slone et al. | 73/38 |
| 3,371,520 | 3/1968 | Slone et al. | 73/38 |
| 3,707,870 | 1/1973 | Herve et al. | 73/38 |
| 3,882,714 | 5/1975 | Libal et al. | 73/38 |
| 4,203,317 | 5/1980 | Gupta | 73/38 |

*Primary Examiner*—Gerald Goldberg
*Assistant Examiner*—Joseph W. Roskos
*Attorney, Agent, or Firm*—Lerner, David, Littenberg & Samuel

[57] ABSTRACT

An apparatus for porosimetric measurements, wherein a sample to be analyzed is put in an ampoule filled with mercury and submitted to ever increasing pressures, in order to obtain measurements of the mercury volume variations due to pressure increases.

Such mercury volume variations, which are correlated to the sample pore sizes, are detected by measuring capacity variations in a mercury condenser provided for in a capillary neck of ampoule.

7 Claims, 3 Drawing Figures

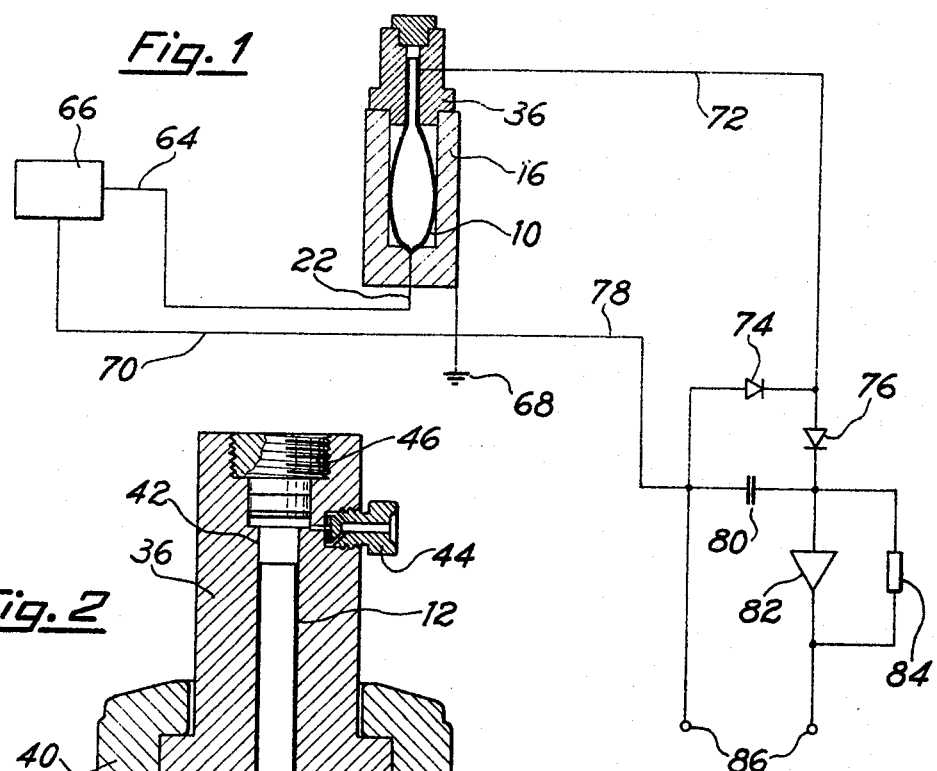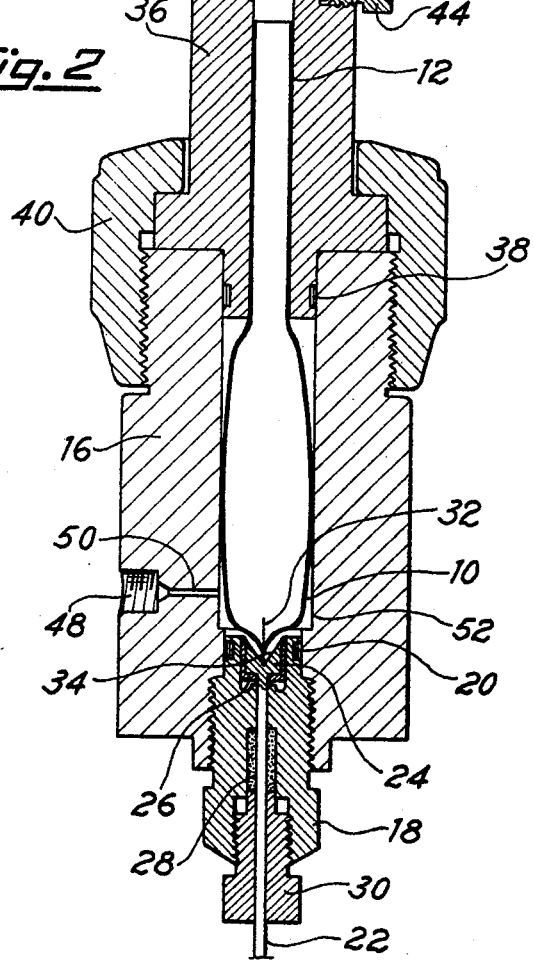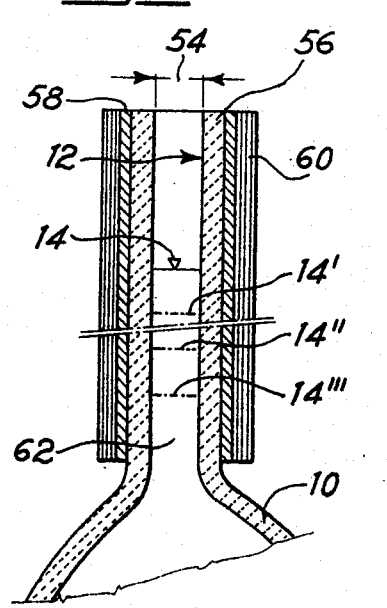

APPARATUS FOR POROSIMETRIC MEASUREMENTS

BACKGROUND OF THE INVENTION

1. Field of the Invention

This invention relates to a so-called porosimeter, that is a measuring apparatus capable of recording volume and size of superficial microcavities, or pores, in solid substances, establishing a biunivocal correspondence, at least per points, between a determined average radius dimension of pores and their volume. In other words, the apparatus is capable of determining the volume of the solid pores having a certain average radius and, subsequently, the volume of the pores having ever lower average radius.

2. Description of the Prior Art

Similar apparatuses are already known and operate according to the so-called Drake method, which essentially consists in placing the solid under test into a vessel, creating vacuum in this vessel, filling same with mercury and submitting mercury to ever increasing pressures. For each specific pressure valve it is possible to establish an average radius of the pores into which mercury penetrates. In other words, each pressure value corresponds to a value of the pores average radius, above which pores are filled with mercury, while mercury, on the contrary, does not penetrate into pores having lower average radius.

This average radius value is given by the following relation:

$$Rm = (2\sigma \cos \theta)\alpha/p$$

where:
- $Rm$ = average radius of pores, in A;
- $\sigma$ = mercury vapour tension at 25° C. (temperature at which analysis is carried out);
- $\theta$ = contact angle between mercury and material under test. This angle is known for any material and has a value of approx. 140°, anyway always ranging between 130° and 150°;
- $p$ = pressure exerted.

It is therefore obvious that, knowing $\sigma$ and $\theta$ values and measuring p value, it is easy and automatic to correlate p to Rm and obtain the latter value from easy knowledge of p, exactly measurable by means of any suitable known system. In order to obtain the required biunivocal correlation between the pores volume and the relevant average radius Rm, it is then necessary to perform, for each Rm value, that is for each p value, an exact measurement of mercury volume variations in the vessel. In fact, as mercury is an incompressible liquid, each decrease in Hg volume which can be recorded outside, of course involves the introduction of an equivalent Hg volume into the pores of the solid under test. The tendency is to obtain a continuous curve (today achievable only by extrapolation of points), correlating the values of volume and average radius of pores. In the practical application of this method, the above mentioned vessel is constitued by an ampoule, for instance a glass one, which is housed in an autoclave where a suitable liquid is introduced, partly also penetrating into the ampoule mouth. Once the autoclave is closed, said liquid is put under pressure with increasing values, to which negative variations in the ampoule mercury volume correspond, measured in correlation with the different pressure values.

The main problem faced up to now in the application of the described Drake method resulted to be the measurement of the above mentioned mercury volume variations in the ampoule. In the known apparatuses of this kind, it has been attempted to solve the problem by using a capillary of strictly constant diameter in correspondence with the ampoule neck and measuring the level variations of mercury in this capillary. In the known apparatuses, the latter measurement is carried out by connecting the ampoule bottom, by means of a metal probe crossing it, to an electric source, using a dielectric liquid for filling the autoclave and closing the electrical circuit by means of the mercury in the ampoule and a contact needle penetrating into the capillary down to the mercury level. The contact needle is mounted on a support which is made rotate in a threaded seat so that each turn of the support corresponds to one lead of the needle to which a certain mercury volume variation corresponds, measurable on the basis of the capillary diameter.

The analysis is carried out in subsequent steps, making the needle advance as far as the memory level and closure of the electrical circuit, then stopping the needle and increasing pressure until the circuit opens due to mercury meniscus lowering, interrupting pressure increase and making the needle advance again to repeat the cycle until pressure maximum values are reached.

From what reported herein, it is already possible to see which are the main disadvantages of the known apparatuses working as described above. First of all, measuring precision is strictly related to the precision achieved in the needle progress, and the instrument construction is very complex and expensive, involving numerous drawbacks in the use, especially due to the need of obtaining perfect sealing in correspondence to a movable component, such as the contact needle, capable of resisting to the very high pressures involved, which may reach values of 2000-2500 atmospheres. Secondly, considering that the volume variations in question are nonetheless minimum, measurement accuracy is far from being satisfactory. Further more, this accuracy is negatively affected by the possibility that mercury in the ampoule undergoes superficial oxidation, which modifies meniscus formed in such a way that, when the latter is taken away from the needle, the contact is not interrupted, this completely altering measurement result. Finally, measuring is carried out, as described, in a non-continuous system, allowing to obtain only a series of points which must then be extrapolated to obtain a Volume-Average Radius curve, which complicates and furtherly delays analysis already requiring very long time due to the described sequence of steps.

SUMMARY OF THE INVENTION

That being stated, this invention now proposes a new porosimeter, always working according to the above mentioned Drake method and on the basis of the measurement of mercury level variations in the capillary forming the vessel neck, in which the drawbacks of the known apparatuses are avoided and, in particular, the measurement of said level variations is performed without any movable component. Therefore, the above mentioned constructive drawbacks are immediately eliminated and moreover, as will be better shown later on, measuring can be carried out with great rapidity, in continuous cycle, with much higher accuracy without any danger that mercury surface oxidation affects it, and moreover with easy possibility of data digital display.

According to the invention, these and other advantages are obtained by means of an apparatus for porosimetric measurements of the type comprising a vessel housing the solid to be analysed immersed into mercury, adapted to be submitted to controlled pressure increases, said vessel including means for electrically connecting mercury with outside and being provided with a mouth consisting of a gauged-diameter capillary, wherein the mercury meniscus is present at any pressure condition during measurement, characterized in that at least said capillary is constituted by dielectric material, has walls with gauged thickness and is externally surrounded by an armature of electrically conductive material, which is connected, at the outside of the zone submitted to pressure and jointly with said mercury electric connection means, in a circuit including a power source and an instrument measuring capacity variations of the mercury condenser constituted, in the capillary, by mercury, the armature and the dielectric part of the capillary itself.

As a matter of fact, it has been noticed that this mercury condenser and the recording of the capacity variations of same allow to obtain, besides the solution of the above mentioned contructive problems thanks to the elimination of movable components crossing the interface between high pressure zone and atmospheric pressure zone, an accuracy in measuring mercury volume variations 50 to 400 times higher than in the known apparatuses and not affected by possible oxidation of mercury meniscus.

Moreover, measuring may be carried out with considerable rapidity and above all in continuity, giving the possibility of directly obtaining continuous curves Average radius-Pore volume and consequently characteristic curves or porosity spectra of the different substances.

When, according to the already known technique, the vessel is constituted by a glass ampoule placed in an autoclave filled with suitable liquid, it is particularly important that said liquid has a constant dielectric behaviour at any pressure and, in this respect, it has been noticed that the use of common dielectric oil for transformers has proved to be particularly suitable.

BRIEF DESCRIPTION OF THE DRAWINGS

FIG. 1 is a scheme of the apparatus for porosimetric measurements according to this invention.

FIG. 2 is an axial section of the autoclave and the ampoule housed in it, for carrying out porosimetric measurements.

FIG. 3 is a partial section, in magnified scale, of the neck or mouth of the measuring ampoule.

DESCRIPTION OF THE PREFERRED EMBODIMENT

With reference to the drawing and following the already mentioned Drake method, the cited porosimetric measurements are carried out by placing the specimen to be analysed into a vessel, consisting for instance of an ampoule 10 made of glass or other suitable material, in which vacuum is created; then mercury is introduced up to a preset level in correspondence to the relevant substantially capillary-shaped mouth 12. Said level is indicated in FIG. 3 by 14.

Still according to the known technique, the ampoule 10 is placed into an autoclave better shown in FIG. 2 and essentially constituted by a body 16 sealed by a lower fitting 18, with gaskets 20, which is airtightly crossed by an electrode 22 electrically connected to a cone-shaped seat 24 supported by the lower fitting 18 and electrically insulated, as shown in 26, from the same. As illustrated, the electrode 22 axially crosses the lower fitting 18 and the sealing in correspondence to the same is ensured by a packing gland 28 and a screwed union 30. The bottom of ampoule 10 is crossed by a conductor 32 connecting the mercury contained in the ampoule with the electrode 22 through a mercury drop 34 placed in the cone-shaped seat of element 24. As it is shown, the ampoule 10 is inserted into the autoclave body 16, which is closed on its upper part by means of a head 36 provided with sealing 38 and removably blocked in position by means of a screwable nut 40. In correspondence to the upper end of its axial opening 42, the head 36 is provided with a device 44 for air breathing, which can be manually screwed and unscrewed to allow air outlet through the same and respectively to seal the autoclave internal volume. The opening 42 of the autoclave head 36 fits on the mouth or neck of the ampoule 10.

Contrary to the known apparatuses, the head 36 of the autoclave can be closed in its upper part, in construction or by means of a suitable closing system, this avoiding problems caused by the need of maintaining sealing through having a movable component such as the contact needle of the known equipments. In the shown embodiment 46 indicates a threaded seat to insert a sealing element allowing to bring outside the electrical connection necessary to determine mercury volume variations in the ampoule 10, as it will be better described later on. This sealing element, which can be inserted into seat 46, may be of the same type as the one provided at the autoclave bottom and previously described, or of any other known type suitable to support high pressures involved, considering that the electrical connection must be insulated with respect to body 16 and head 36 of the autoclave, but in no case movable parts are taken into consideration.

The illustrated autoclave has in its body 16 a fitting 48, connected through a connector 50 to the internal cavity 52 of same and externally connectable to a device (not illustrated) to supply the cavity 52 of the autoclave with liquid under pressure. In carrying out porosimetric measurements according to Drake method, once the ampoule 10 is introduced into the autoclave and the latter is closed, a suitable liquid is blown into it, fills the whole autoclave cavity around the ampoule 10 and penetrates into the mouth 12 of the latter as far as the level of the mercury meniscus 14 is reached. During this introduction of liquid, the air present in the autoclave is completely discharged through breathing valve 44, which is then closed. After the preliminary operation, the measuring stage is immediately started by increasing the pressure of the liquid introduced through fitting 48 and simultaneously recording mercury volume variations in the ampoule 10 by measuring the lowering of meniscus 14 at different levels 14', 14'', 14''', in correspondence to increasing pressure values. By correlating the pressure valves and the different decreasing levels of the mercury meniscus 14, it is possible to obtain, using suitable transformation formulae, a series of values representing the average radius of pores and the corresponding volume of same, as previously stated. To carry out the above mentioned measurements, according to the invention, an ampoule 10 is used, the mouth 12 of which, besides having an exactly gauged internal diameter 54, presents a wall 56 in a dielectric material, of exactly gauged thickness, surrounded by a metal armature 58 in such a way that between the ampoule-contained mercury 62, the dielectric 56 and the metal armature 58, a mercury condenser is formed, the capacity of which obviously varies according to the position of the meniscus 14 in the capillary 12. The outside of the metal armature 58 in provided with a layer 60 in antifriction material, preferably polytetrafluoroethylene, for better positioning the ampoule in the opening of the autoclave head 36.

In order that said measure of volume or of mercury level 14 in the ampoule 10 is accurate and reliable, it is clear that, besides the gauging conditions of the capillary diameter 54 and the wall 56 thickness of same, other conditions be necessarily checked, and precisely it is necessary that the material forming wall 56 and in general ampoule 10, preferably constituted by glass, results to have good stability at any temperature and pressure; moreover, it is necessary that the liquid filling the autoclave and penetrating the ampoule mouth until reaching said meniscus 14 is a dielectric liquid with constant properties at any pressure and namely from atmospheric pressure up to 2000-2500 atmospheres. In this respect, it has been surprisingly noticed that a particularly suitable liquid is constituted by dielectric oil for transformers, of the commercially available type.

To measure capacity variations of the above mentioned condenser 62, 56, 58, the invention presents a circuit of the type schematically illustrated in FIG. 1 According to this figure, the electrode 22 is connected, through a conductor 64, to a power source 66 consisting in a square-wave oscillator, the other outlet of which is grounded in 68 through a conductor 70, together with the autoclave body 16. The mercury condenser armature 58 is connected, through a conductor 72, to diodes 74 76 which in turn are connected through a conductor 78 to the oscillator 66, so that said mercury condenser and the diodes 74, 76 form a so-called diode pump, constituting a well-known circuit component commonly used for frequency-voltage conversion. In this particular use, the frequency of the square-wave oscillator 66 is constant, while the condenser capacity varies according to the level variations of the meniscus 14. An integration condenser 80 makes continuous the current which is supplied to a negative feedback (84) amplifier 82, so that at the terminals 86 it is possible to obtain voltage value which is directly proportional to the capacity of the previously cited mercury condenser. The use of a diode pump for this measurement is not critical, but particularly advantageous as it allows to solve in a cheap and functional way the problem of "ward" that is the elimination of eddy capacities which might affect the measurement value.

After what has been stated, the advantages of the new porosi-meter according to the invention now result obvious and are hereafter recalled. First of all, the presence of movable contact elements to measure the mercury level in the ampoule capillary 12 is avoided. Secondly, detection may be carried out in continuous cycle with the possibility of immediately tracing average radius-pore volume curves and with a much higher speed than the one allowed by the known equipments. Moreover, the measure accuracy is not affected by the possible oxidation of mercury meniscus and is much higher than that of the known apparatuses. In fact, it is possible to succeed in recording current variations up to tenths of microampere, while a 1/10 mm variation in height of the meniscus 14 may correspond to 17 microamperes. Therefore, it is calculated to obtain accuracy 50 to 400 times greater than that of the apparatuses known up to now. Finally, the data obtained at terminals 86 as an analogue signal of voltage varying from 0 to 10 volt, may be easily converted, by means of an analogue/digital converter, into a suitable digital form.

Finally, it has to be noticed that, through a preferred realisation of the invention has been illustrated and described, however it may undergo to numerous changes and variations, such as will result obvious to those skilled in the art, without departing from the spirit and scope of this invention.

We claim:

1. Apparatus for porosimetric measurements comprising a vessel for housing a solid to be analysed, said solid being immersed in mercury and suitable for being subjected to controlled pressure increases, said vessel including a neck portion taking the form of a gauged-diameter capillary where a mercury meniscus forms at any pressure condition during the measurement, said gauged-diameter capillary being formed of dielectric material and having walls exhibiting a gauged thickness, armature means formed of electrically conductive material externally surrounding said neck, means for electrically communicating through said vessel with mercury present therein, and means for connecting said armature means outside zones subjected to pressure and said electrically communicating means in a circuit including a power source and means for measuring capacity variations of a mercury condenser formed in said capillary between said mercury and said armature and the dielectric wall of said capillary.

2. The apparatus according to claim 1 wherein said vessel takes the form of a glass ampoule housed in an autoclave and said autoclave is filled with a liquid, partly penetrating into said neck of said vessel which may be subjected to controlled increases in pressure, said liquid manifesting constant dielectric properties at any pressure condition during measuring operations.

3. The apparatus according to claim 2, wherein said liquid is a dielectric oil for transformers.

4. The apparatus according to claim 1, wherein said capillary is made of a glass stable at any temperature.

5. The apparatus according to claim 4, wherein said armature means is externally covered by a layer made of antifriction material to facilitate positioning of said capillary in said autoclave.

6. The apparatus according to claim 1, wherein said electrical power source takes the form of a square-wave oscillator and said mercury condenser results in a circuit supplied by said square-wave oscillator and a diode pump formed by a plurality of diodes and operating at fixed frequency and variable capacity.

7. The apparatus according to claim 6, wherein said means for measuring comprises said diode pump, an integration condenser, a negative feedback amplifier and terminal means at which a difference of potential proportional to the capacity of said mercury condenser may be recorded.

* * * * *

UNITED STATES PATENT AND TRADEMARK OFFICE
CERTIFICATE OF CORRECTION

PATENT NO. : 4,272,983
DATED : June 16, 1981
INVENTOR(S) : Giorgio Sisti, et als It is certified that error appears in the above-identified patent and that said Letters Patent are hereby corrected as shown below:

Column 1, line 33, "Rm=(2σcosθ)α/p" should read $$--Rm = \frac{2 \sigma \cos \theta}{p}--$$

Signed and Sealed this

Eighth Day of September 1981

[SEAL]

Attest:

GERALD J. MOSSINGHOFF

Attesting Officer

Commissioner of Patents and Trademarks